United States Patent [19]

Wang et al.

[11] Patent Number: 4,918,239

[45] Date of Patent: Apr. 17, 1990

[54] METHOD OF PRODUCING CYCLOHEXANONE FROM CYCLOHEXANOL THROUGH OXIDATIVE DEHYDROGENATION

[75] Inventors: Ikai Wang; Yu-Ming Lin, both of Hsinchu, Taiwan

[73] Assignee: National Science Council, Taipei, Taiwan

[21] Appl. No.: 289,680

[22] Filed: Dec. 27, 1988

[51] Int. Cl.$^4$ .............................................. C07C 45/51
[52] U.S. Cl. ................................... 568/360; 568/361; 568/363
[58] Field of Search ................ 568/360, 361, 402, 363

[56] References Cited

U.S. PATENT DOCUMENTS

| | | | |
|---|---|---|---|
| 1,460,876 | 7/1923 | Williams | 568/402 |
| 1,988,481 | 1/1935 | Cardarelli | 568/402 |
| 2,051,266 | 8/1936 | McAllister et al. | 568/402 |
| 2,092,870 | 9/1937 | Beamer | 568/402 |
| 3,974,221 | 8/1976 | Duggan | 568/360 |
| 4,154,762 | 5/1979 | Huang et al. | 568/360 |
| 4,250,121 | 2/1981 | Mimoun | 568/360 |
| 4,670,605 | 6/1987 | Chiu et al. | 568/361 |
| 4,816,606 | 3/1989 | Brenner et al. | 568/360 |

FOREIGN PATENT DOCUMENTS 960160  9/1982  U.S.S.R. ............................. 562/402

*Primary Examiner*—James H. Reamer
*Attorney, Agent, or Firm*—Bacon & Thomas

[57] ABSTRACT

This invention provides a method for producing cyclohexanone from cyclohexanol using oxidative dehydrogenation. More particularly, this invention comprises adding a certain amount of a gaseous oxidant to the cyclohexanol feed stream; and, converting the cyclohexanol to cyclohexanone over a CuO-ZnO catalyst.

7 Claims, 2 Drawing Sheets

METHOD OF PRODUCING CYCLOHEXANONE FROM CYCLOHEXANOL THROUGH OXIDATIVE DEHYDROGENATION

BACKGROUND OF THE INVENTION

Since the commercial process of producing Nylon-6,6 is in the market since 1939, polyamide resins have become more important than ever in man-made fibers and engineering plastics. The two major raw materials in producing polyamide fiber are caprolactam and adipic acid. The main application of caprolactam is in the production of Nylon-6. Adipic acid is used to make Nylon-6,6. Caprolactam can be obtained by the oximation of cyclohexanone. Adipic acid is made through the oxidation of cyclohexanone. Therefore, cyclohexanone is the major intermediate in the production of caprolactam and adipic acid.

In the industry, there are two major methods for preparing cyclohexanone. One is the dehydrogenation of cyclohexanol to cyclohexanone after the hydrogenation of phenol to cyclohexanol. The other one is the subsequent hydrogenation of benzene to cyclohexane. The cyclohexane is oxidized producing cyclohexanol and a small portion of cyclohexanone. The cyclohexanol is then dehydrogenated to cyclohexanone The conventional method used in the dehydrogenation of cyclohexanol to cyclohexanone is the direct dehydrogenation reaction as shown in (a):

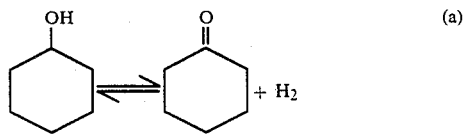

This conventional method has two major disadvantages; (1) unless the temperature is raised, the conversion of cyclohexanol is severely constrained by the thermodynamic equilibrium because the Gibbs free energy is almost zero at the reaction temperature of 227° C.; (2) the reaction is highly endothermic (at 227° C., H=+15.8 kcal/mole), that a high operation cost and expensive shell and tube reactor are needed.

The primary purpose of this invention is to provide an alternative method for the production of cyclohexanone from cyclohexanol without having those two mentioned disadvantages. To achieve this purpose, this invention provides a method of adding a gaseous oxidant in the cyclohexanol feed steam and catalytically converts the cyclohexanol to cyclohexanone. The catalyst used in this invention is the conventional Cu-Zn oxide catalyst. With the addition of this gaseous oxidant in the cyclohexanol feed stream, the reaction heat of the catalytic dehydrogenation of cyclohexanol to cyclohexanone is almost zero. Therefore, an inexpensive insulated reactor can be used in this reaction.

SUMMARY OF THE INVENTION

The present invention is concerned with a method for producing cyclohexanone from cyclohexanol using oxidative dehydrogenation. More particularly, this invention comprises adding a suitable amount of a gaseous oxidant to the cyclohexanol feed stream, and converting the cyclohexanol to cyclohexanone in the presence of a CuO-ZnO catalyst.

Due to the gaseous oxidant in the feed, instead of direct dehydrogenation of cyclohexanol to cyclohexanone, some of the cyclohexanol go through an oxidative dehydrogenation, as shown in (b):

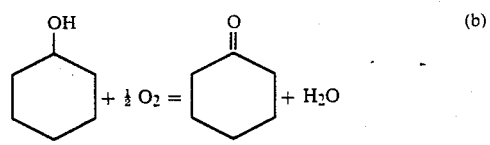

Comparing reaction (b) to reaction (a), there are two advantages of reaction (b) over reaction (a): (1) the Gibbs free energy is reduced (at 227° C., G=−52.0 kcal/mole), so that the equilibrium conversion is increased; (2) there is a change in the reaction, from endothermic to exothermic (at 227° C., H=−42.5 kcal/mole); therefore there is no need to supply heat during the reaction. Furthermore, by properly adjusting the amount of gaseous oxidant in the cyclohexanol feed stream, the summation of heat formations from reaction (a) and (b) can be tuned to zero. This will result in the saving of capital investment in the reactor, because the relatively expensive tube and shell type reactor is not necessary.

DETAILED DESCRIPTION OF THE INVENTION

Figure 1:
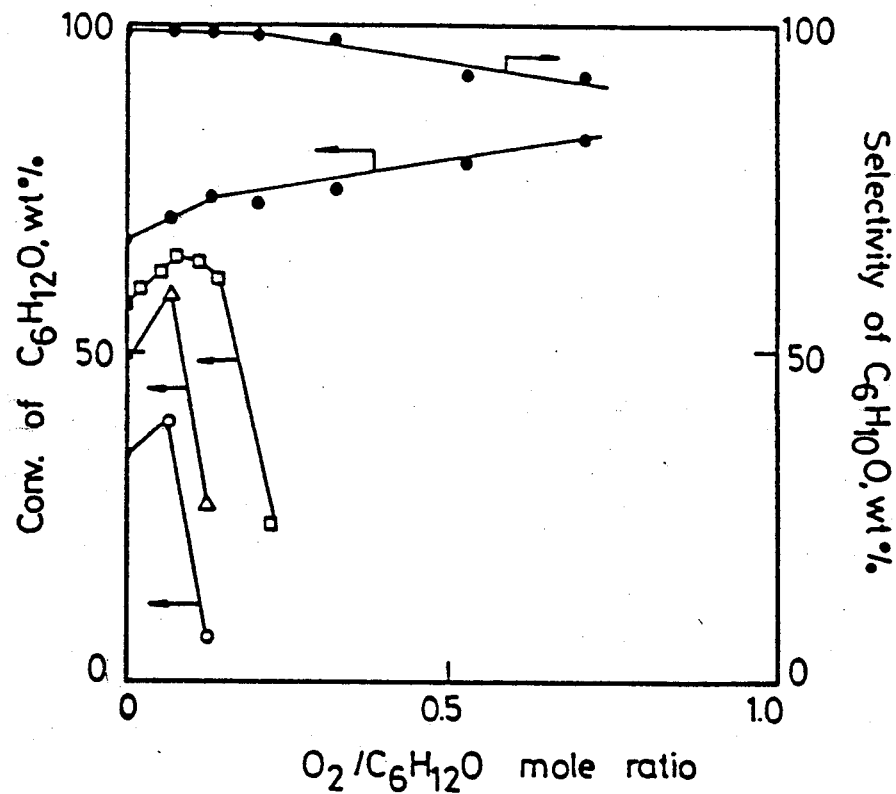
FIG. 1 is a plot which shows the effect of oxygen to cyclohexanol mole ratio on oxidative dehydrogenation of cyclohexanol, in which each point was taken at a time-on-stream of 4 hrs. Reaction conditions: T, 240 C; Re, 0.37; conc., 0.02 mol/L; LHSV (●)0.5 $h^{-1}$, (□)5 $h^{-1}$, (△)10 $h^{-1}$, (○)20 $h^{-1}$.

Commercial catalyst used in the direct dehydrogenation of cyclohexanol are mainly CuO-MgO or CuO-ZnO. It has been reported in the literature that the conversion of cyclohexanol using CuO-MgO or CuO-ZnO at 240° C.-260° C. is about 43%-64%, and its selectivity to cyclohexanone is close to 100%. The conversion is raised to 75%-86% at a temperature of 300° C.-320° C., and its selectivity is about 98.3%-99.4% to cyclohexanone. However, to prevent the copper base catalyst from sintering and thereby shortening the life of the catalyst, the reaction temperature must be limited to below 280° C., which severely constrains the conversion of cyclohexanol due to thermodynamic equilibrium. The conventional method of direct dehydrogenation is highly endothermic. Inorder to maintain the reaction temperature so as to keep the conversion levels, the space velocity of the cyclohexanol is so limited (between 0.5-1.0 $hour^{-1}$) that the productivity is confined. By adding a gaseous oxidant in the cyclohexanol feed stream, the conventional direct dehydrogenation process could be changed to an oxidative dehydrogenation process. There would be three significant advantages over the conventional direct dehydrogenation process: (1) a higher conversion could be obtained because the equilibrium conversion of direct dehydrogenation is no longer the limit of the new oxidative dehydrogenation process; (2) by properly adjusting the amount of the gaseous oxidant and partially converting hydrogen to water, a change of thermal effect could be attained. Thus an improvement of productivity in the conventional dehydrogenation can be achieved; and (3) the energy consumption could be reduced because the in-situ burning of hydrogen would eliminate the need to supply heat externally.

In this invention, the oxidative dehydrogenation of cyclohexanol to cyclohexanone, it was found out that the $CuO$-$ZnO$-$Al_2O_3$ catalyst is even more stable than the $CuO$-$ZnO$ or $CuO$-$MgO$ catalyst in the oxidative dehydrogenation process. Especially, the catalyst having a Cu-Zn mole ratio of about 1:2 and 5-10 mole% of Al is the most stable one. It was also found that the stability of using the $CuO$-$ZnO$-$Al_2O_3$ catalyst to the gaseous oxidant could be raised, if a variety of oxides including sodium oxide, potassium oxide, palladium oxide or HPA (heteropoly acid) were impregnated on the $CuO$-$ZnO$-$Al_2O_3$ catalyst.

In this invention, the gaseous oxidant includes oxygen and air. The oxygen to cyclohexanol mole ratio is below 0.2, preferably below 0.15.

In this invention, the reaction was carried out under the same conditions as the conventional direct dehydrogenation process. The concentration of cyclohexanol feed stream is from 0.01 to 0.04 mole/L. The reaction temperature is between 180° C.-270° C. The space velocity of cyclohexanol is less than 20 volume/volume-hour.

In order that those skilled in the art may readily understand this process, the following examples are given by ways of illustration and not by ways of limitation.

EXAMPLE 1

A Cu-An-Al oxide catalyst was prepared in this example. 1 mole/L of Copper, Zinc and Aluminum nitric solution were prepared individually. After mixing the proper ratios of the above three solutions for 30 minutes, the resulting mixture was heated to about 50° C.-60° C. 1 mole/L of ammonium carbonate solution was then added, with stirring, into the metal nitric mixture in a ratio of 150 mL/hr until the pH of the mixture reached 7. The agitation was maintained for another 1.5 hours.

The above mixture was filtered and the cake was then washed with de-ionized water. The washed cake was then dried at 110° C. for 8 hours. After drying, the powder was calcined for 3 hours at 300° C. The resulting metal oxide powder after calcination was then reduced in hydrogen to form the catalyst. This resulting catalyst is the catalyst used in this invention for cyclohexanol oxidative dehydrogenation.

EXAMPLE 2

This example illustrates how the product was manufactured and shows its material balance examination.

| Reaction conditions | |
|---|---|
| composition of catalyst (mole %) | Cu:Zn:Al = 31:64:5 |
| catalyst reduction temperature | 220° C. |
| catalyst reduction period | 4.5+ hours |
| concentration of cyclohexanol in feed | 0.02 mole/L |
| space velocity of cyclohexanol feed | 0.5 volume/volume-hr |
| Reynold Number | 0.37 |

Table 1 shows the experimental results of oxidative dehydrogenation of cyclohexanol at various reaction conditions. As the oxygen to cyclohexanol mole ratio is greater than zero, part of the product (cyclohexanone) was formed through reaction (b). By examining the amount of oxygen being consumed and the amount of water being formed, it has been proven that part of the reaction go through reaction (b). As shown in Table 1, the reaction heat changes from a positive value (endothermic) to a negative value (exothermic), as the oxygen to cyclohexanol mole ratio increases. It was also found that the reaction heat is close to zero at the condition where the oxygen to cyclohexanol mole ratio is 0.07. At this mole ratio, the reactor needs only insulation instead of supplying heat externally. Therefore, the equipment and operating cost is reduced. At the present tube and shell reactor set-up, the space velocity of cyclohexanol can be increased to improve productivity without decreasing the in-situ temperature of the reactor.

TABLE 1

| Reaction temperature, °C. | 240 | | | 200 | | |
|---|---|---|---|---|---|---|
| Oxygen/cyclohexanol, mole ratio | 0.000 | 0.070 | 0.135 | 0.000 | 0.060 | 0.116 |
| Mass of reactor feed, g | | | | | | |
| Liquid phase | | | | | | |
| Cyclohexanol | 8.97 | 8.97 | 8.97 | 8.97 | 8.97 | 8.97 |
| Vapor phase | | | | | | |
| Nitrogen | 2.51 | 2.37 | 2.24 | 2.52 | 2.04 | 1.93 |
| Oxygen | — | 0.20 | 0.39 | — | 0.17 | 0.33 |
| Total Mass, g | 11.48 | 11.54 | 11.60 | 11.49 | 11.18 | 11.23 |
| Mass of reactor effluent, g | | | | | | |
| Liquid phase | | | | | | |
| Cyclohexanol | 2.87 | 2.61 | 2.33 | 5.07 | 4.96 | 4.57 |
| Cyclohexanone | 5.89 | 6.17 | 6.47 | 3.71 | 4.07 | 4.30 |
| Cyclohexene | 0.014 | 0.013 | 0.026 | — | — | 0.005 |
| Heavy End | 0.035 | 0.045 | 0.029 | 0.013 | 0.006 | 0.007 |
| Water | — | 0.22 | 0.40 | — | 0.10 | 0.34 |
| Vapor phase | | | | | | |
| Nitrogen | 2.51 | 2.37 | 2.24 | 2.52 | 2.04 | 1.93 |
| Oxygen | — | 0.007 | 0.019 | — | 0.006 | 0.012 |
| Hydrogen | 0.117 | 0.106 | 0.095 | 0.078 | 0.063 | 0.053 |
| Carbon Dioxide | — | — | 0.027 | — | — | 0.014 |
| Total Mass, g | 11.436 | 11.541 | 11.636 | 11.391 | 11.245 | 11.231 |
| Total Mass Balance, wt % | 99.65 | 100.13 | 100.38 | 99.22 | 101.32 | 100.11 |
| Oxygen Mass Balance, wt % Calculated Cyclohexanol | — | 102.68 | 102.85 | — | 97.03 | 98.52 |

TABLE 1-continued

| Reaction temperature, °C. | | 240 | | | 200 | |
|---|---|---|---|---|---|---|
| Conversion (Direct Dehydrogenation), wt % | 65.39 | 59.24 | 53.10 | 43.59 | 35.27 | 29.62 |
| Calculated Cyclohexanol Conversion (Oxidative Dehydrogenation), wt % | — | 13.79 | 24.96 | — | 11.27 | 21.30 |
| Calculated Total Conversion, wt % | 65.39 | 73.03 | 78.06 | 43.59 | 46.54 | 50.92 |
| Measured Cyclohexanol Conversion, wt % | 67.43 | 70.48 | 73.74 | 42.39 | 45.09 | 48.55 |
| Calculated Heat of Reaction (kcal/mole of converted cyclohexanol) | +15.86 | +4.70 | −3.04 | +15.86 | +1.57 | −8.84 |

EXAMPLE 3

This example illustrates the effect of the catalyst compositions on the activity and stability of oxidative dehydrogenation of cyclohexanol.

| Reaction conditions | |
|---|---|
| catalyst reduction temperature | 220° C. |
| reaction temperature | 240° C. |
| catalyst reduction period | 4.5+ hours |
| concentration of cyclohexanol in feed | 0.02 mole/L |
| space velocity of cyclohexanol feed | 5 volume/volume-hr |
| Reynold Number | 0.37 |

As shown in Table 2, the optimum conversion is when the Cu-Zn ratio is approximately 2; while when the aluminum content in the catalyst is 5%–10%, the catalyst shows optimal activity and stability. From Table 2, it was found that the conversion of cyclohexanol would reach a maximum and gradually decline as the oxygen to cyclohexanol mole ratio increases in the feed.

TABLE 2

| Catalyst compositions, mole % | | | cyclohexanol conversion, wt % oxygen/cyclohexanol, mole ratio | | | | | |
|---|---|---|---|---|---|---|---|---|
| | Cu | Zn | Al | 0.00 | 0.08 | 0.13 | 0.18 | 0.23 | 0.28 |
| (a) | 0 | 100 | 0 | 6.65 | 1.43 | — | — | — | — |
| (b) | 14 | 86 | 0 | 61.44 | 64.73 | 65.70 | 54.88 | — | — |
| (c) | 33 | 67 | 0 | 65.45 | 67.74 | 72.82 | 69.03 | 63.92 | — |
| (d) | 50 | 50 | 0 | 38.79 | 37.46 | 4.27 | — | — | — |
| (e) | 67 | 33 | 0 | 29.14 | 28.20 | 4.33 | — | — | — |
| (f) | 86 | 14 | 0 | 49.33 | 43.57 | — | — | — | — |
| (g) | 100 | 0 | 0 | 38.86 | 28.74 | — | — | — | — |
| (h) | 33 | 65 | 2 | 49.28 | 46.26 | 5.45 | — | — | — |
| (i) | 33 | 62 | 5 | 67.17 | 69.64 | 71.82 | 71.69 | 69.37 | 61.27 |
| (j) | 30 | 60 | 10 | 65.28 | 69.87 | 70.03 | 57.13 | — | — |

EXAMPLE 4

This example demonstrates the effect of the oxygen to cyclohexanol mole ratio in the feed stream on the conversion of cyclohexanol.

| Reaction conditions | |
|---|---|
| catalyst reduction temperature | 220° C. |
| catalyst reduction period | 4.5+ hours |
| composition of catalyst | Cu:Zn:Al = 31:64:5 |
| reaction temperature | 240° C. |
| concentration of cyclohexanol in feed | 0.02 mol/L |
| space velocity of cyclohexanol feed | 0.5–20 volume/volume-hr |
| Reynold number | 0.37 |

FIG. 1 shows that under the low oxygen to cyclohexanol mole ratio, for example below 0.08, the cyclohexanol conversion increases along with the increase of oxygen to cyclohexanol mole ratio regardless of various space velocities (from 0.5–20 volume/volume-hr). Its selectivity is above 99% as well. Therefore, there is an optimal oxygen to cyclohexanol mole ratio; that the catalyst performs very well in both activity and selectively. Thus, the stability operation of catalyst is related to the oxygen content in the feed. Therefore, the catalyst with the highest oxygen to cyclohexanol ratio which still gives high selectivity and stable operation is the most stable.

EXAMPLE 5

The effect of space velocity on the optimal oxygen to cyclohexanol mole ratio in the feed is shown in this example.

| Reaction conditions | |
|---|---|
| composition of catalyst | Cu:Zn:Al = 31:64:5 |
| catalyst reduction temperature | 220° C. |
| catalyst reduction period | 4.5+ hours |
| reaction temperature | 240° C. |
| concentration of cyclohexanol in feed | 0.02 mole/L |
| Reynold number | 0.37 |

Figure 2:
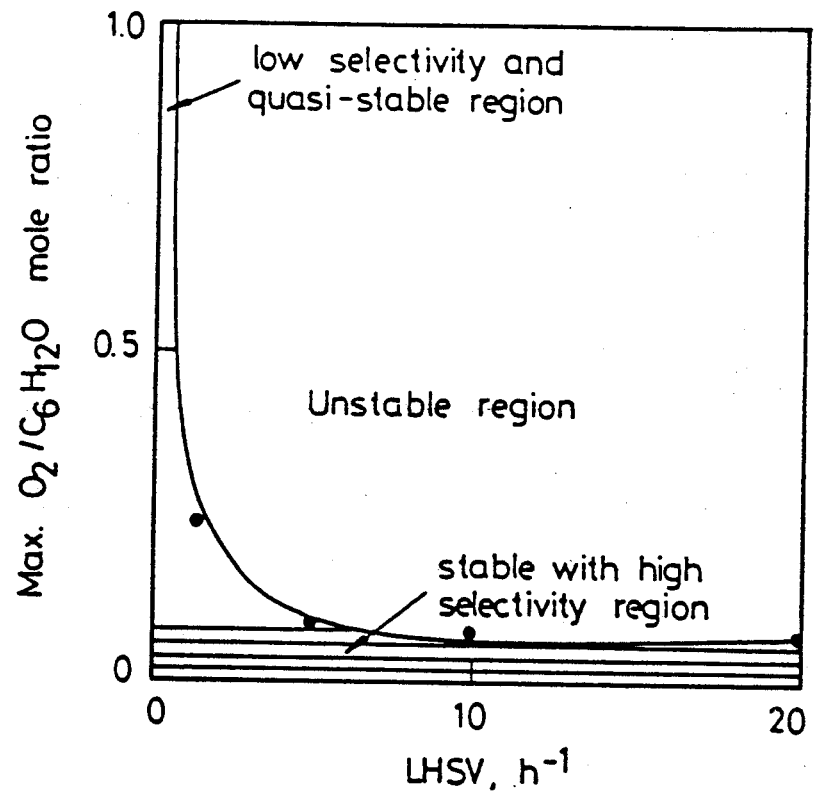
FIG. 2 is a plot which shows the relation of optimal mole ratio of oxygen to cyclohexanol with LHSV.

The experimental results were shown in FIG. 2. The oxidative dehydrogenation of cyclohexanol was carried out with high selectivity and stability at low oxygen to cyclohexanol mole ratios (shaded region in FIG. 2). Comparing with results from Example 2, it was found out that the adiabatic reaction took place in the shaded area. Above the shaded region, the left side was classified as low selectivity and quasi-stable region; the right side was the region for unstable operation.

EXAMPLE 6

This example illustrates the effect of reaction temperature on the optimal oxygen to cyclohexanol mole ratio.

| Reaction conditions | |
|---|---|
| catalyst reduction temperature | 220° C. |
| catalyst reduction period | 4.5+ hours |
| space velocity of cyclohexanol | 5 volume/volume-hr |

-continued

| Reaction conditions | |
|---|---|
| feed cyclohexanol concentration in the feed | 0.03 mole/L |
| Reynold number | 0.8 |
| Catalyst concentration | Cu:Zn:Al = 31:64:5 |

Table 3 lists the outcome of this experiment. Using the stable operation of the catalyst (at optimal oxygen to cyclohexanol mole ratio) as the basis for comparison, the increase in reaction temperature also increases the optimal oxygen to cyclohexanol mole ratio as well as the cyclohexanol conversion.

TABLE 3

| Reaction temperature, °C. | 180 | 200 | 240 | 270 |
|---|---|---|---|---|
| Optimal oxygen to cyclohexanol mole ratio | 0.06 | 0.06 | 0.09 | 0.19 |
| Cyclohexanol conversion, % | 38.5 | 49.5 | 65.0 | 85.0 |

EXAMPLE 7

In this example, the effect of the Reynold number on the oxidative dehydrogenation of cyclohexanol to cyclohexanone is discussed.

| Reaction conditions | |
|---|---|
| catalyst reduction temperature | 220° C. |
| catalyst reduction period | 4.5+ hours |
| reaction temperature | 240° C. |
| cyclohexanol space velocity in the feed | 5 volume/volume-hr |
| Cyclohexanol concentration in the feed | 0.02 mole/L |
| composition of catalyst | Cu:Zn:Al = 31:64:5 |

TABLE 4

| Reynold number | 0.37 | 0.08 | 1.47 |
|---|---|---|---|
| Optimal oxygen to cyclohexanol mole ratio | 0.08 | 0.06 | 0.04 |
| Cyclohexanol conversion, wt % | 64.5 | 69.5 | 70.0 |

As shown in Table 4, a decrease of Reynold number will increase the optimal oxygen to cyclohexanol mole ratio.

EXAMPLE 8

This example shows the influence of cyclohexanol concentration in the feed stream on the performance of cyclohexanol oxidative dehydrogenation.

| Reaction conditions | |
|---|---|
| catalyst reduction temperature | 220° C. |
| catalyst reduction period | 4.5+ hours |
| reaction temperature | 240° C. |
| space velocity of cyclohexane | 5 volume/volume-hr |
| Reynold number | 0.37 |
| catalyst composition | Cu:Zn:Al = 31:64:5 |

TABLE 5

| Cyclohexanol concentration | 0.01 | 0.02 | 0.03 |
|---|---|---|---|
| Optimal oxygen to cyclohexanol mole ratio | 0.06 | 0.08 | 0.10 |
| Cyclohexanol conversion, % | 76.0 | 64.5 | 61.0 |

The experimental results indicate that the optimal oxygen to cyclohexanol mole ratio increases as the cyclohexanol concentration in the feed stream increases.

EXAMPLE 9

This example demonstrates the test of life of the catalyst.

| Reaction conditions | |
|---|---|
| catalyst reduction temperature | 220° C. |
| catalyst reduction period | 4.5+ hours |
| reaction temperature | 270° C. |
| space velocity of cyclohexanol | 1 volume/volume-hr |
| cyclohexanol concentration in the feed | 0.025 mole/L |
| oxygen to cyclohexanol mole ratio | 0.12 |
| Reynold number | 0.37 |
| catalyst composition | Cu:Zn:Al = 31:64:5 |

TABLE 6

| Reaction time, hrs | 80 | 100 | 300 |
|---|---|---|---|
| Cyclohexanol conversion, wt % | 82.5 | 79.5 | 80.5 |

The data listed in Table 6 clearly indicate that the catalyst does not show any deactivation after 300 hours of operation time.

EXAMPLE 10

In this example, the effect of impregnation of palladium oxide on the catalyst on the oxidative dehydrogenation is pointed out.

| Reaction conditions | |
|---|---|
| impregnated material | Pd(NO$_3$)$_2$ |
| loading of palladium atom, wt % | 0-0.15 |
| catalyst reduction temperature | 220° C. |
| catalyst reduction period | 4.5+ hours |
| reaction temperature | 240° C. |
| space velocity of cyclohexanol feed | 5 volume/volume-hr |
| concentration of cyclohexnol in feed | 0.02 mole/L |
| Reynold number | 0.8 |
| catalyst composition | Cu:Zn:Al = 31:64:5 |

Table 7 lists the experiment results under various palladium loading in the catalyst. Increase of palladium loading will also increase the optimal oxygen to cyclohexanol mole ratio and the cyclohexanol conversion under the optimal ratio.

TABLE 7

| Palladium loading in the catalyst, wt % | 0.00 | 0.15 | 0.15 |
|---|---|---|---|
| Optimal oxygen to cyclohexanol mole ratio | 0.00 | 0.12 | 0.23 |
| Cyclohexanol conversion, wt % | 64.5 | 69.5 | 75.5 |

EXAMPLE 11

The effect of the modification of CuO-ZnO-Al2O3 via heteropoly acid (HPA) on oxidative dehydrogenation was demonstrated in this example. The experimental conditions were identical to those used in example 10 except that the impregnated material was changed from palladium oxide to HPA, whose impregnated loading was from 0-10 wt%. Table 8 lists the experimental results. The impregnation of HPA showed a positive effect of optimal oxygen to cyclohexanol mole ratio at low loading (below 5%), and had a negative effect at high loading (above 5%). The conversion of cyclohexanol under these various loading of HPA also showed the same trend as the optima; oxygen to cyclohexanol mole ratio.

TABLE 8

| HPA loading in the catalyst, wt % | 0 | 2 | 5 | 10 |
|---|---|---|---|---|
| Optimal oxygen to cyclohexanol mole ratio | 0.08 | 0.12 | 0.17 | 0.12 |
| Cyclohexanol conversion, wt % | 64.5 | 67.0 | 72.0 | 54.0 |

EXAMPLE 12

In this example, the effect of impregnation of $K_2CO_3$ and $Na_2CO_3$ on the catalyst on the oxidative dehydrogenation is demonstrated. The results are listed on Table 9.

| Reaction conditions | |
|---|---|
| impregnated materials | $Na_2CO_3$, $K_2CO_3$ |
| loading of impregnated material, wt % | 1 |
| catalyst reduction temperature | 220° C. |
| catalyst reduction period | 4.5+ hours |
| reduction temperature | 240° C. |
| space velocity of cyclohexanol feed | 1.5 volume/volume-hr |
| cyclohexanol concentration in the feed | 0.022 mole/L |
| Reynold number | 1.1 |
| catalyst composition, mole ratio | Cu:Zn:Al = 31:64:5 |

TABLE 9

|  | CuO—ZnO—$Al_2O_3$ | wt % $N_2$/CuO—ZnO—$Al_2O_3$ | wt %K/CuO—ZnO—$Al_2O_3$ |
|---|---|---|---|
| Optimal oxygen to cyclohexanol mole ratio | 0.20 | 0.29 | 0.29 |
| Cyclohexanol conversion | 75.23 | 75.15 | 74.10 |

We claim:
1. In a method for producing cyclohexanone by catalytic dehydrogenation of a cyclohexanol feed stream containing cyclohexanol and an oxygen containing gaseous oxidant; wherein the improvement comprises selecting a mole ratio of oxygen to cyclohexanol in the feed stream which is less than 0.2; and dehydrogenating the cyclohexanol feed stream in the presence of a CuO-ZnO-$Al_2O_3$ catalyst having a composition of Cu from 10-60 mole percent, Zn from 30-90 mole percent, and Al from 0-10 mole percent; and said dehydrogenation being conducted at a temperature of 180°-280° C.
2. The method of claim 1 wherein the oxygen-containing gaseous oxidant is oxygen or air.
3. The method of claim 1 wherein the mole ratio of Cu:Zn is about 1:2, and the mole percent of Al is from 5-10.
4. The method of claim 1 wherein the catalyst is impregnated with pallidium oxide or heteropoly acid.
5. The method of claim 3 wherein the catalyst is impregnated with palladium oxide or heteropoly acid.
6. The method of claim 1 wherein the dehydrogenation reaction conditions are: a space velocity of cyclohexanol feed below 20 volume/volume-hr; the cyclohexanol concentration in the feed is below 0.04 mole/L; and the Reynolds number is below 1.5.
7. The method of claim 6 wherein the air to cyclohexanol mole ratio in the feed stream is less than 0.8.

* * * * *